(12) United States Patent
Fogliato et al.

(10) Patent No.: US 7,728,126 B2
(45) Date of Patent: Jun. 1, 2010

(54) PURIFICATION OF BETA-LACTAM PRODUCTS

(75) Inventors: Giovanni Fogliato, Barzana (IT); Marco Forzatti, Monza (IT); Maurizio Zenoni, Paullo (IT)

(73) Assignee: ACS DOBFAR S.p.A., Tribiano (IT)

( * ) Notice: Subject to any disclaimer, the term of this patent is extended or adjusted under 35 U.S.C. 154(b) by 890 days.

(21) Appl. No.: 11/465,283

(22) Filed: Aug. 17, 2006

(65) Prior Publication Data

US 2007/0093657 A1   Apr. 26, 2007

(30) Foreign Application Priority Data

Oct. 20, 2005   (IT) .......................... MI2005A1991

(51) Int. Cl.
*C07D 501/57* (2006.01)
*C07D 501/12* (2006.01)

(52) U.S. Cl. ...................................... 540/221; 540/222

(58) Field of Classification Search ................ 540/220, 540/221

See application file for complete search history.

(56) References Cited

U.S. PATENT DOCUMENTS 3,594,371 A * 7/1971 McIntyre ................... 540/220
4,485,235 A * 11/1984 Katano et al. .............. 540/221
2007/0027314 A1 * 2/2007 Manca et al. .............. 540/228

OTHER PUBLICATIONS

E. M. Gordon, et al. "Sulfenyl Transfer Rearrangement of Sulfenimines (Thiooximes). A Novel Synthesis of 7-Alpha-Methoxycephalosporins and 6-Alpha-Methoxypenicillins", Journal of the American Chemical Society, XP-002413255, vol. 102, No. 5, Feb. 27, 1980, pp. 1690-1702.

H. E. Applegate, et al. "Synthesis of 7-Alpha-Methoxycephalosporins", Journal of Organic Chemistry, XP-002413256, vol. 39, No. 18, 1974, pp. 2794-2796.

Timothy Jen, et al. "A Stereospecific Synthesis of C-6(7) Methoxypenicillin and -Cephalosporin Derivatives", Journal of Organic Chemistry, XP-002413257, vol. 38, No. 16, 1973, pp. 2857-2859.

Ronald W. Ratcliffe, et al. "Total Synthesis of Beta-Lactam Antibiotics III. (+/−) -Cefoxitin", Tetrahedron Letters, No. 46, 1973, pp. 4653-4656.

* cited by examiner

*Primary Examiner*—Mark L Berch
(74) *Attorney, Agent, or Firm*—Oblon, Spivak, McClelland, Maier & Neustadt, L.L.P.

(57) ABSTRACT

Method for purifying 7α-methoxy-cephalosporins containing as impurity the corresponding 7α-methylthio analogue, which is transformed into its methoxy analogue by treatment with a halogenating agent in methanol. In this way the complete conversion of the sulphurated impurity into the corresponding methoxy analogue is obtained.

11 Claims, No Drawings

PURIFICATION OF BETA-LACTAM PRODUCTS

BACKGROUND OF THE INVENTION

1. Field of the Invention

7α-methoxy-cephalosporins are a particular class of cephalosporins having a methoxy group in position 7α. This methyl group confers marked stability against the action of various β-lactams, for which reason certain representatives of this cephalosporin class have entered into clinical use. The most well known are cefoxitin, cefmetazol and cefotetan, however 6α-methoxy-penicillin and 7α-methoxy-oxacephalosporin homologues also exist.

2. Discussion of the Background

The process used for introducing the methoxy group into position 7α of cephalosporins and 6α of penicillins is hence of evident importance. U.S. Pat. No. 4,109,084, U.S. Pat. No. 4,158,657, U.S. Pat. No. 4,154,927 and U.S. Pat. No. 4,119,778 claim methods for preparing cephalosporin thiooximes characterised by the $R_1$—S—N=group in position 7. In particular, U.S. Pat. No. 4,119,778, U.S. Pat. No. 4,154,927 and U.S. Pat. No. 4,158,657 claim penicillin and cephalosporin thiooximes in which a (1-methyl-1H-tetrazol-5-yl) thiomethyl is also present in position 3, and a method for their preparation starting from 6-APA, 7-ADCA, 7-ACA and derivatives; in the case in point, the said tetrazole group is a substituent of the cefmetazol molecule, one of the 7α-methoxy-cephalosporins which have long entered into clinical use.

The 7α-methoxy nuclei can be obtained from these thiooximes by treatment with triphenylphosphine and a suitable catalyst in the presence of methanol. The 7α-methoxy nuclei obtained in this manner are then transformed into the corresponding acylamino derivatives, i.e. into the 7β-acylamino-7α-cephalosporins or into the relative intermediates for their preparation.

Unfortunately, the aforesaid process has the drawback of providing a product which is impure because of the presence of 7α-methylthio derivatives, as described in J.A.C.S. 1980, 120, pp 1690-1702, originating from a transposition of the —SH$_3$ group of an intermediate adduct linked to triphenylphosphine. The impurity is obviously entrained into the subsequent steps of the synthesis leading to 7α-methoxy-cephalosporins, with the result that these latter are contaminated by the sulphurated impurity.

SUMMARY OF THE INVENTION

The main object of the present invention is eliminate the thio compound from the initial steps of the process, to also prevent useless wastage of reactants consumed for transforming the sulphurated derivatives.

This object is attained by a process for converting into 7α-methoxy-cephalosporins 7α-methylthio-cephalosporins contained as impurities in quantities of 0.5% or less in the 7α-methoxy-cephalosporins, characterised in that a 7α-methoxy-cephalosporin containing an amide group in position 7, and impure with the corresponding 7α-methylthio analogue, is treated with a halogenating agent chosen from the group consisting of bromine, N-bromosuccinimide, N-chlorosuccinimide, N-chloroacctamide, chloramine T, dichlorourethane and 1,3-dibromo-5,5-dimethylhydantoin, in methanolic solution, at a temperature between 0° and +5° C. for a time between 30 minutes and 3 hours, to obtain the complete conversion of the sulphurated impurity into the corresponding methoxy analogue.

Preferably the halogenating agent is N-bromosuccinimide or bromine. With the aforesaid acylation of the 7β-amino-7α-methoxy nuclei, an intermediate is obtained contaminated with methylthio derivative, which is surprisingly transformed into the corresponding methoxy derivative, enabling a final product to be obtained which is free from methylthio analogue.

The value of the invention is greatly increased by the fact that the halogenating agents used in the aforesaid new process have already been used in β-lactam chemistry, but with a quite separate effect than that now demonstrated, hence it was unexpected that these should give rise to the reaction utilized according to the invention. In this respect, it is well known that NBS and NCS are used in transforming penicillin sulphoxides (U.S. Pat. No. 4,052,387, U.S. Pat. No. 4,159,266) into azetidinone sulphinyl halides and that these can also be used for halogenating 3-methyl-cefem derivatives to give 3-halo-methyl-cefem analogues which are then transformed into 3-hexomethylene-cefam derivatives (U.S. Pat. No. 4,985,554, U.S. Pat. No. 4,994,454).

DETAILED DESCRIPTION OF THE INVENTION

The following examples serve only to illustrate the invention without however limiting it.

Example 1

Benzhydryl 3-[(1-methyl-1H-tetrazol-5-yl)thio]methyl-7α-methoxy-7β-bromoacetamido-3-cefem-4-carboxylate 20 g of benzhydryl 3-[(1-methyl-1H-tetrazol-5-yl)thio] methyl-7α-methoxy-7β-bromoacetamido-3 cefem-4-carboxylate containing 0.5% of 7α-methylthio derivative are dissolved in 120 ml of methylene chloride. 3.6 ml of pyridine are added, the mixture cooled to −30° C. and 8.73 g of bromoacetylbromide are added. The mixture is maintained under agitation for 1 hour between −30° C. and −20° C., then washed twice with 40 ml of water between 0° C. and +5° C. 50 ml of methanol are added then 1 g of N-bromosuccinimide, maintaining the temperature between 0° C. and +5° C. After 60 minutes of reaction the organic phase is washed with 65 ml of a 1.5% aqueous sodium thiosulphate solution while maintaining the temperature less than 10° C. The organic phase is again washed with 65 ml of water, concentrated under vacuum and the oily residue taken up with 150 ml of methanol. The mixture is maintained under agitation for 30 minutes at ambient temperature, then the crystalline product is filtered off and washed with methanol.

20 g of the product indicated in the title are obtained free from traces of 7α-methylthio derivative.

Example 2

Benzhydryl 3-[(1-methyl-1H-tetrazol-5-yl)thio]methyl-7α-methoxy-7β-bromoacetamido-3-cefem-4-carboxylate 20 g of the product indicated in the title but containing 0.2% of 7α-methylthio derivative are dissolved in a mixture of 100 ml of methylene chloride and 40 ml of methanol at ambient temperature. The mixture is cooled to between 0° C. and +5° C., 0.45 g of bromine diluted in 5 ml of methylene chloride are added and allowed to react for 2 hours. The reaction mixture is washed with a solution of 2 g of sodium thiosulphate in 100 ml of water, then washed with water alone and the organic phase concentrated under reduced pressure. The oily residue is taken up with 200 ml of methanol and maintained under agitation for 30 minutes at ambient temperature. The solid obtained is filtered off and washed with methanol.

Yield: 18 g of the product indicated in the title, free from 7α-methylthio derivative.

Example 3

Benzhydryl 3-[(1-methyl-1H-tetrazol-5-yl)thio]methyl-7α-methoxy-7β-bromoacetamido-3-cefem-4-carboxylate 20 g of the product indicated in the title but containing 0.2% of 7α-methylthio derivative are dissolved in a mixture of 100 ml of methylene chloride and 40 ml of methanol at ambient temperature. The mixture is cooled to between 0° C. and +5° C., 0.5 g of N-bromosuccinimide are added and allowed to react for 2 hours. The reaction mixture is washed with a solution of 2 g of sodium thiosulphate in 100 ml of water, then washed with water alone and the organic phase concentrated under reduced pressure. The oily residue is taken up with 200 ml of methanol and maintained under agitation for 30 minutes at ambient temperature. The solid obtained is filtered off and washed with methanol.

Yield: 18 g of the product indicated in the title, free from 7α-methylthio derivative.

By operating in a like manner to Examples 1, 2 and 3, but using N-chlorosuccinimide, N-chloroacetamide, chloramine T, dichlorourethane and 1,3-dibromo-5,5-dimethylhydantoin instead of N-bromosuccinimide or bromine, the 7α-methylthio derivative impurity is likewise converted into the 7α-methoxy analogue.

What is claimed is:

1. A process for converting into 7α-methoxy-cephalosporins 7α-methylthio-cephalosporins contained as impurities in the 7α-methoxy-cephalosporins, wherein a 7α-methoxy-cephalosporin containing an amide group in position 7, and impure with 0.5% of the corresponding 7α-methylthio analogue, is treated with a halogenating agent chosen from the group consisting of bromine, N-bromosuccinimide, N-chlorosuccinimide, N-chloroacetamide, chloramine T, dichlorourethane and 1,3-dibromo-5,5-dimethylhydantoin, in methanolic solution, at a temperature between 0° and +5° C. for a time between 30 minutes and 3 hours, to obtain the complete conversion of the sulphurated impurity into the corresponding methoxy analogue.

2. The process as claimed in claim 1, wherein the halogenating agent is N-bromosuccinimide.

3. The process as claimed in claim 1, wherein the halogenating agent is bromine.

4. A process of making a 7α-methoxy-cephalosporin compound, comprising:

contacting a 7α-methylthio-cephalosporin compound having an amide group in position 7 with at least one halogenating agent selected from the group consisting of bromine, N-bromosuccinimide, N-chlorosuccinimide, N-chloroacetamide, chloramine T, dichlorourethane and 1,3-dibromo-5,5-dimethylhydantoin at a temperature of from 0 to 5° C. for a period between thirty minutes to three hours, wherein, prior to said contacting, said 7α-methylthio-cephalosporin compound is present, as an impurity, in a mixture with a 7α-methoxy-cephalosporin compound in an amount of 0.5 wt % or less, and said at least one halogenating agent is present in a methanolic solution.

5. The process as claimed in claim 4, wherein the halogenating agent is N-bromosuccinimide.

6. The process as claimed in claim 4, wherein the halogenating agent is bromine.

7. The process as claimed in claim 4, wherein the halogenating agent is N-chlorosuccinimide.

8. The process as claimed in claim 4, wherein the halogenating agent is N-chloroacetamide.

9. The process as claimed in claim 4, wherein the halogenating agent is chloramine T.

10. The process as claimed in claim 4, wherein the halogenating agent is dichlorourethane.

11. The process as claimed in claim 4, wherein the halogenating agent is 1,3-dibromo-5,5-dimethylhydantoin.

* * * * *